United States Patent
Wan et al.

(10) Patent No.: US 10,537,593 B2
(45) Date of Patent: Jan. 21, 2020

(54) **METHOD, TARGET AND APPLICATION FOR NO ACCUMULATION TO DECREASE *PSEUDOMONAS AERUGINOSA* INVASIVENESS**

(71) Applicants: Microbiology Institute of Shaanxi, Xi'an (CN); Institute of Biophysics, Chinese Academy of Sciences, Beijing (CN)

(72) Inventors: Yi Wan, Xi'an (CN); Chang Chen, Beijing (CN); Lei Gao, Xi'an (CN); Yuying Zhang, Beijing (CN); Xinhua Qiao, Beijing (CN); Yan Wang, Xi'an (CN)

(*) Notice: Subject to any disclaimer, the term of this patent is extended or adjusted under 35 U.S.C. 154(b) by 0 days.

(21) Appl. No.: 15/770,469

(22) PCT Filed: Oct. 22, 2016

(86) PCT No.: PCT/CN2016/102973
§ 371 (c)(1),
(2) Date: Apr. 23, 2018

(87) PCT Pub. No.: WO2017/067516
PCT Pub. Date: Apr. 27, 2017

(65) Prior Publication Data
US 2018/0311275 A1    Nov. 1, 2018

(30) Foreign Application Priority Data
Oct. 23, 2015  (CN) .......................... 2015 1 0697439

(51) Int. Cl.
*A61K 33/26*    (2006.01)
*A61P 31/04*    (2006.01)
*A61K 33/00*    (2006.01)

(52) U.S. Cl.
CPC .............. *A61K 33/00* (2013.01); *A61K 33/26* (2013.01); *A61P 31/04* (2018.01)

(58) Field of Classification Search
CPC .......... A61K 33/00; A61K 33/26; A61P 31/04
See application file for complete search history.

(56) References Cited

PUBLICATIONS

Gao et al 2016, RedoxBiology, 8: 252-258 (Year: 2016).*
Barraud et al 2009, Journal of bacteriology, vol. 191, No. 23, p. 7333-7342 (Year: 2009).*
Turkoz et al 1998, European journal of ophthalmology, vol. 8, No. 3, pp. 137-141 (Year: 1998).*
Barraud et al 2006, Journal of Bacteriology, vol. 188, No. 21, pp. 7344-7353. (Year: 2006).*

* cited by examiner

*Primary Examiner* — Padmavathi Baskar
(74) *Attorney, Agent, or Firm* — Novoclaims Patent Services LLC; Mei Lin Wong (57) ABSTRACT

Provided are a method, target and application for NO accumulation to decrease invasiveness of *Pseudomonas aeruginosa*; achieving NO accumulation by means of external NO donors or disruption of internal NO metabolism in an environment where *Pseudomonas aeruginosa* is growing or being cultured, in order to decrease production by *Pseudomonas aeruginosa* of the invasion factor pyocyanin. Utilizing even micro-quantities of NO can significantly inhibit *Pseudomonas aeruginosa* PCN (PCN synthesis down 82% with 60 μM SNP treatment); by inhibiting NO reductase, an enzyme related to NO metabolism, PCN synthesis can be significantly inhibited (the PAO1-Δnor strain has 84% PCN reduction). Using NO donors or inhibiting enzymes involved in *Pseudomonas aeruginosa* NO metabolism as a means of combating bacterial infectious disease does not affect the body's normal microflora like traditional antibiotics.

9 Claims, 7 Drawing Sheets

METHOD, TARGET AND APPLICATION FOR NO ACCUMULATION TO DECREASE *PSEUDOMONAS AERUGINOSA* INVASIVENESS

CROSS REFERENCE OF RELATED APPLICATION

This is a national phase national application of an international patent application number PCT/CN2016/102973 with a filing date of Oct. 22, 2016, which claimed the priority of application number 201510697439.9 with a filing date of Oct. 23, 2015 in China. The contents of these specifications, including any intervening amendments thereto, are incorporated herein by reference.

BACKGROUND OF THE PRESENT INVENTION

Field of Invention

The present invention relates to biomedicine technology, and more particularly to a method of NO (Nitric Oxide) accumulation for reducing the invasiveness and target point of *Pseudomonas aeruginosa* and its application thereof.

Description of Related Arts

*Pseudomonas aeruginosa* (PA) is an important opportunistic pathogen, and is considered to be one of the three lethal bacteria of hospital infectious diseases. In the case of low human immunity, for example, people suffering from chronic diseases, patients with organ transplantation or patients with large-area burns and the like, it can cause different acute or chronic infection and even lead to death, especially to patients with sensitive immune system and patients with cystic fibrosis (CF); more than 80% of CF patients die from these infections. *Pseudomonas aeruginosa* has strong resistance to most antibiotics (cephalosporins, penicillins, fluoroquinolones, and aminoglycoside antibiotics). At present in clinical, the antibiotics only target to protein synthesis, cell walls, DNA replication, cell membrane, folic acid coenzyme and etc., the limitations are due to drug resistance. The invasiveness of bacteria refers to its ability to infect and cause disease, and the invasiveness of bacteria depends on the virulence factors produced by the bacteria and the mechanism of damage. The pathogenic bacteria destroy the normal physiological functions of the host cell by releasing a variety of toxin proteins and even lead to the cell death. In recent years, research studies have shown that the invasiveness of bacteria can be used as a target point to develop new antibiotic, that bacterial infection diseases can be treated by inhibiting the pathogenicity of bacteria. Since there is no effect on bacteria growth, bacterial drug resistance caused by traditional antibiotics can be reduced or avoided.

Pyocyanin (PCN) is an important invasive factor of *Pseudomonas aeruginosa*. PCN is a blue phenazine compound that can penetrate through a biological membrane easily and is commonly found in the sputum of CF patients infected by *Pseudomonas aeruginosa*. Recent animal model experiments showed that PCN is a key compound in the infection process of *Pseudomonas aeruginosa*, and its virulence can significantly reduce the number of cells in target tissues and organs, while PCN can also inhibit ciliary peristalsis of respiratory epithelial cells and increase intracellular peroxide production. It has been reported that some compounds can inhibit the synthesis of PCN of *Pseudomonas aeruginosa* to various degrees. For example, catechin (2~4 mM) can reduce the synthesis of PCN by 50%; eugenol (50~400 μm) can reduce the synthesis of PCN by 56%; Yunnan Baiyao (2.5 g/l) can reduce the synthesis of PCN by 76.5%. However, many of these compounds have problems of high drug dosage and low efficiency in inhibiting the synthesis of PCN, and many of them have strong bactericidal properties themselves, which will not only increase the drug resistance of the strain, but also affect the growth of the normal flora in the human body and cause damage to human health.

Flagella is another important invasive factor of *Pseudomonas aeruginosa*. Flagella is a fibroinous adhesin that readily adheres to the intima. Adhesion is the first step for pathogens to contact and infect cells and is closely related to pathogenicity. The completion of the adhesion process is mainly caused by the action of adhesin. Adhesins are special structures and related proteins that exist on the surface of bacteria, which facilitate the bacteria to adhere to host cells. The flagella make *Pseudomonas aeruginosa* have chemical tropism on the matrix, so that the cells can perform an unorganized movement on the surface of the liquid medium with low viscosity, that is swimming motility, and another kind of exercise performed on the viscous semi-solid medium of the water sample, that is, swarming motility. Flagella-mediated movement helps bacteria to increase nutrient availability, escape toxic substances, transfer to appropriate hosts, and find proper fixation sites, so flagella-mediated movement is another important invasive factor of *Pseudomonas aeruginosa*.

SUMMARY OF THE PRESENT INVENTION

An object of the present invention is to provide a method of NO (Nitric Oxide) accumulation for reducing the invasiveness and target point of *Pseudomonas aeruginosa* and its application thereof. From the perspective of "reducing the invasiveness of bacteria", a new way to effectively inhibit *Pseudomonas aeruginosa* invasiveness factors is realized. Its related drug targets can be applied to the preparation of drugs.

The present invention is implemented by the following technical solutions:

A method of reducing invasiveness of *Pseudomonas aeruginosa*, under a living environment or a culture environment of *Pseudomonas aeruginosa*, achieving NO accumulation through exogenous NO donor or endogenous NO metabolism blockage, thereby reducing the production of the invasiveness factor of pyocyanin of *Pseudomonas aeruginosa*;

reducing the mediated motility of flagella and fimbriae of *Pseudomonas aeruginosa* simultaneously.

The exogenous NO donor comprises a compound capable of directly or indirectly supplying NO to *Pseudomonas aeruginosa*, the exogenous NO donor is present in the living or culture environment of *Pseudomonas aeruginosa*.

The control of the endogenous NO metabolism blockage includes inhibition, blocking, or enhancement of NO metabolism-related enzymes.

The endogenous NO metabolism blockage refers to: cloning a plasmid or vector that is capable of recombining with NO metabolism-related enzymes and causing loss of function of NO metabolism-related enzymes into *Pseudomonas aeruginosa*; or employing inhibitors of NO metabolism-related enzymes their enzyme activity such that the activities of enzymes are reduce or lost to achieve NO accumulation in *Pseudomonas aeruginosa*; Or employing genetic recombination or agonists to enhance the enzymes that favor the production of endogenous NO to achieve NO accumulation in *Pseudomonas aeruginosa*.

A target that can promote the reduction of the invasiveness of *Pseudomonas aeruginosa*, the target includes intracellular gene locus associated with NO metabolism in *Pseudomonas aeruginosa* and enzymes associated with NO metabolism;

The gene locus associated with NO metabolism, the enzymes associated with NO metabolism are inhibited or activated to achieve NO accumulation, thereby reducing the production of the invasiveness factor of pyocyanin of *Pseudomonas aeruginosa* and/or reducing the motility of *Pseudomonas aeruginosa*.

An application of achieving NO accumulation through exogenous NO donor or endogenous NO metabolism blockage to reduce the production of the invasiveness factor of pyocyanin of *Pseudomonas aeruginosa* and/or reduce the motility of *Pseudomonas aeruginosa* under a living environment or a culture environment of *Pseudomonas aeruginosa*.

The application of NO donor compounds in the preparation of a medicament for reducing the invasiveness of *Pseudomonas aeruginosa*.

The use of a plasmid, vector or compound that blocks the NO metabolism of *Pseudomonas aeruginosa* in the preparation of a medicament for reducing the invasiveness of *Pseudomonas aeruginosa*.

The application includes:

The use of NO metabolism-blocking compounds in the form of antagonism, inhibition or blockage of NO metabolism in the preparation of a medicament for reducing the invasiveness of *Pseudomonas aeruginosa*.

The application in the preparation of a medicament for reducing the invasiveness of *Pseudomonas aeruginosa* through a key enzyme molecule in the NO metabolic pathway as a target or an enzyme, a carrier, or a compound of a recombination target.

The application of a medicament or a carrier which utilizes NO metabolism related enzyme of *Pseudomonas aeruginosa*, including NO reductase, nitrate reductase, nitrite reductase and NO synthase, as a target in the preparation of a medicament for reducing an invasiveness of *Pseudomonas aeruginosa*.

The medicament is a drug against pulmonary cystic fibrosis or *Pseudomonas aeruginosa* septicemia.

Compared with the existing arts, the present invention has the following advantageous technical effects:

1) The invention provides a method, target and application for reducing invasiveness of *Pseudomonas aeruginosa* by using NO accumulation. By utilizing a trace amount of NO donor or an endogenous NO accumulation, the biological synthesis of invasiveness factor of *Pseudomonas aeruginosa* is effectively inhibited. That *Pseudomonas aeruginosa* PCN can be realized only by using a trace amount of NO (60 μm SNP treatment, PCN synthesis is reduced by 82%) and has characteristics of high efficiency. Meanwhile, NO accumulation can also influence the mobility mediated by the flagellar and IV-type bacteria of *Pseudomonas aeruginosa*, not only the invasiveness is inhibited, but also the pathogenicity range is reduced, that other methods of killing *Pseudomonas aeruginosa* can be facilitated. Thus this provides a possible new method and a series of drug targets for treating *Pseudomonas aeruginosa* infection.

2) According to the present invention, if the key enzyme Nor of the NO downstream metabolism is inhibited, the same inhibition effect on invasiveness as to the exogenous NO donor is produced (compared a mutant strain with no Nor to a wild strain, the PCN synthesis of the mutant strain is reduced by 84% and the movement of the bacteria can be inhibited). Therefore, the NO metabolism-related enzyme represented by Nor will be an effective target for inhibiting NO accumulation and thus reducing the invasiveness of *Pseudomonas aeruginosa*, and is an effective target for medicament preparation.

3) The NO donor of the present invention, such as sodium nitroprusside (SNP), has been used for clinical trial since 1929, and it is a traditional powerful, rapid vasodilator by itself and so there is no problem in safety. Furthermore, the present invention further confirms that SNP has no antagonistic effect on traditional antibiotics. Given its availability to promote NO accumulation and thereby reduce the invasiveness of *Pseudomonas aeruginosa*, the use of SNP has been expanded to allow it to be used in combination with antibiotics for the preparation of *Pseudomonas aeruginosa* inhibitors.

4) The present invention seeks new antibacterial substances from the perspective of "antibacterial invasiveness". NO, on the premise of non-inhibiting and non-sterilizing bacteria, can inhibit the invasiveness of pathogenic bacteria, does not bring pressure to the bacteria itself, and can reduce or avoid the emergence of drug resistance. Therefore, the use of NO accumulation in the preparation of medicaments to inhibit bacterial infections can help to solve the clinical challenges of drug resistance of bacteria.

5) The present invention utilizes NO donors, or through inhibiting the NO metabolism related enzyme of *Pseudomonas aeruginosa*, as a way to fight bacterial infections, so it will not affect the normal microbial population of the human body like traditional antibiotics, and the human normal microbial population has a very important role in human health.

DETAILED DESCRIPTION OF THE PREFERRED EMBODIMENT

The present invention is described in further detail below with reference to specific embodiments, which is for illustration only and is not intended to be limiting.

The present invention provides a method of reducing invasiveness of Pseudomonas aeruginosa, under a living environment or a culture environment of Pseudomonas aeruginosa, achieving NO accumulation through exogenous NO donor or endogenous NO metabolism control, thereby reducing the production of the invasiveness factor of pyocyanin of Pseudomonas aeruginosa.

The exogenous NO donor comprises a compound capable of directly or indirectly supplying NO to Pseudomonas aeruginosa, the exogenous NO donor is present in the living or culture environment of Pseudomonas aeruginosa. Specifically, the present invention utilizes a trace amount of NO donor to inhibit the biosynthesis of pyocyanin (PCN), which is one of the Pseudomonas aeruginosa invasiveness factors, and can reduce the invasiveness of bacteria without killing the bacteria.

The control of the endogenous NO metabolism includes inhibition, blockage, or enhancement of NO metabolism-related enzymes. The endogenous NO metabolism blockage refers to: cloning a plasmid or vector that is capable of recombining with NO metabolism-related enzymes and causing loss of function of NO metabolism-related enzymes into Pseudomonas aeruginosa; or employing inhibitors of NO metabolism-related enzymes such that the activities of enzymes are reduce or lost to achieve NO accumulation in Pseudomonas aeruginosa; Or employing genetic recombination or agonists to enhance the enzymes that favor the production of endogenous NO to achieve NO accumulation in Pseudomonas aeruginosa.

In particular, NO reductase (Nor), which is related to the accumulation of endogenous NO, is used as the representative element. The effect of this target on the biosynthesis of PCN was studied by constructing mutants lacking Nor. The results showed that the addition of trace amount of NO donor or inhibition target nor can significantly reduce the biosynthesis of pyocyanin of Pseudomonas aeruginosa.

The present invention further provides a target that can promote the reduction of the invasiveness of Pseudomonas aeruginosa, the target includes intracellular gene locus associated with NO metabolism and enzymes associated with NO metabolism in Pseudomonas aeruginosa;

The gene locus associated with NO metabolism, the enzymes associated with NO metabolism are inhibited or activated to achieve NO accumulation, thereby reducing the production of the invasiveness factor of pyocyanin of Pseudomonas aeruginosa.

Based on the above description, the present invention provides an application of achieving NO accumulation through exogenous NO donor or endogenous NO metabolism blockage to reduce the production of the invasiveness factor of pyocyanin of Pseudomonas aeruginosa under a living environment or a culture environment.

Further explanations of the invention are given below:

1) Use of Trace Amount of NO Donors to Effectively Inhibit the Biosynthesis of an Invasiveness Factor of Pseudomonas aeruginosa The Pseudomonas aeruginosa is a conditional pathogen, and the present invention relates to its model strain PAO1 and clinically isolated strain of Pseudomonas aeruginosa.

The invasiveness factor is the secondary metabolite pyocyanin of Pseudomonas aeruginosa, pyocyanin belongs to the phenazine compound and its molecular formula $C_{13}H_{10}N_2O$.

A trace amount of exogenous NO donor is used to inhibit the biosynthesis of pyocyanin of Pseudomonas aeruginosa. The NO donor includes sodium nitroprusside ($Na_2Fe(CN)_5NO$), nitrosoglutathione GSNO ($C_{10}H_{16}N_4O_7S$), and etc.

2) Use of Selective Inhibition of NO Downstream Metabolic Targets to Effectively Inhibit the Biosynthesis of Invasiveness Factor of Pseudomonas aeruginosa The key enzyme for the downstream metabolism of NO in Pseudomonas aeruginosa—the NO-reductase, acts to convert intracellular NO to $N_2O$ so as to avoid negative effect on cells which is caused by excessive NO accumulation.

The selective inhibition is that the mutant strain lacking Nor is constructed by the gene knockout method in the present invention.

Embodiment 1: Determining Significant Inhibition Effect of NO Donor SNP on the Biosynthesis of Pyocyanin of Pseudomonas aeruginosa Through Flat-Plate Culture According to this embodiment, the strain used is the Pseudomonas aeruginosa model strain PAO1 (which is more common, and is available from various collection centers). This bacteria are obligate aerobic bacteria and is culture under 37° C. in common bacteria culture medium (such as LB medium) for 20~24 h.

In this study, the effect of NO on the synthesis of PCN in bacterial cells is investigated through adding multiple sets of flat plate samples of SNPs at different concentrations and one blank flat plate. The final concentrations of SNPs in each group are 20, 40, 60, 80, and 100 μM respectively. After PAO1 is cultured for 22 hours, the PCN produced by the cells in the flat plate is extracted with chloroform, condensed, and then developed with hydrochloric acid, and the level of PCN produced by the cells is determined according to the light absorption value of the coloring solution at 520 nm.

Figure 1:
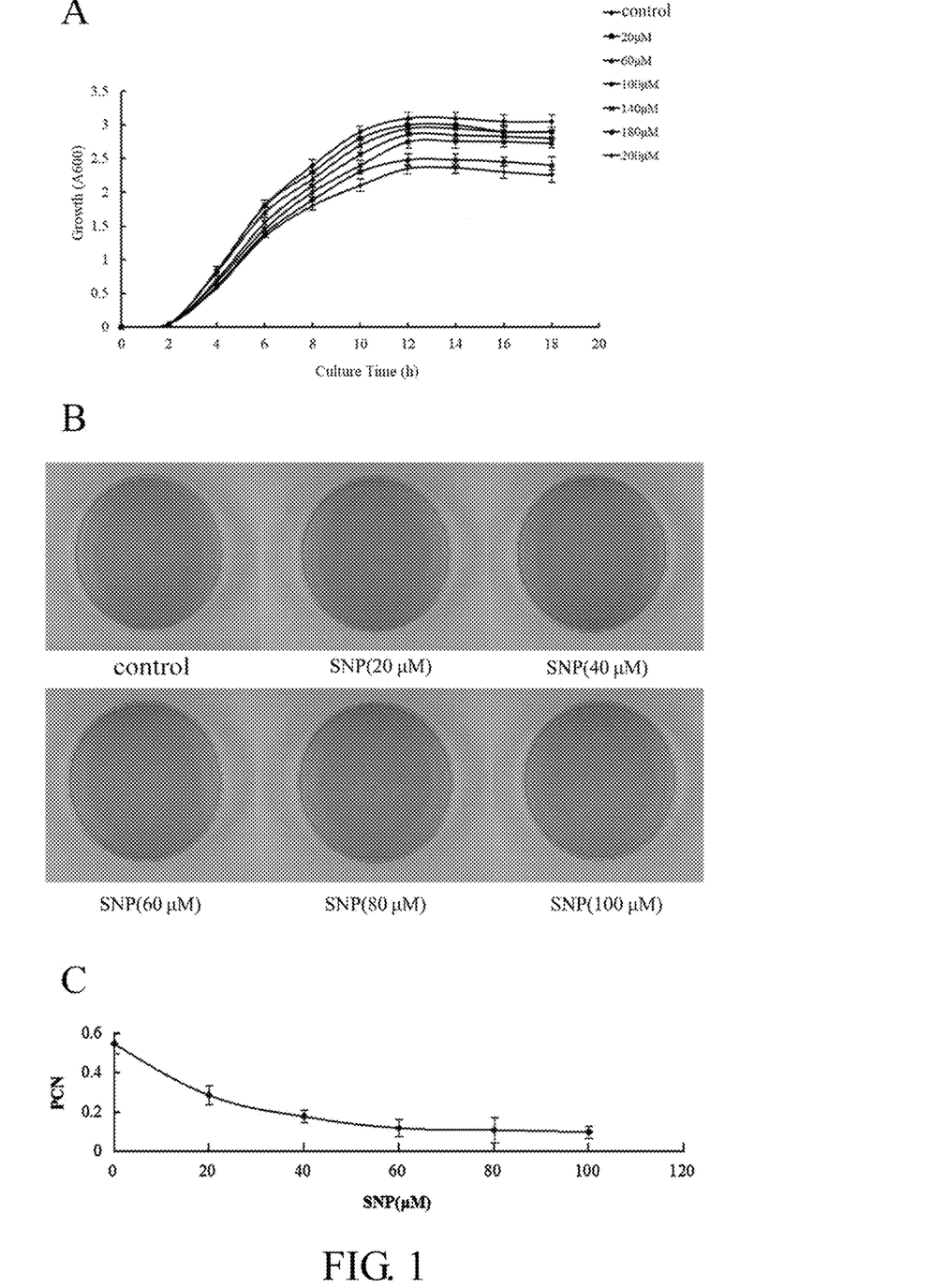
FIG. 1 is an influence of NO donor SNP on growth of PAO1 and synthesis of PCN; (wherein A is the effect of different concentrations of SNP on the growth of PAO1; and B is the effect of different concentrations of SNP on PCN production by PAO1; C is the trend of the effect of different concentrations of SNP on PCN production by PAO1)

The results are shown in FIG. 1. The results showed that as the concentration of SNP in the flat plate increased, the synthesis of PCN from Pseudomonas aeruginosa is reduced significantly, and the trend of reduction of PCN within the concentration range of 20 μM~60 μM is significant. When the concentration is greater than 60 μM, the decrease is flattened. It can be seen that 60 μM is the relatively ideal concentration (shown in C in FIG. 1).

Embodiment 2: Determining Significant Inhibition Effect of SNP on the Biosynthesis of Pseudomonas aeruginosa PCN without Imposing Pressure on the Growth of Bacteria Through Shake Flask Cultivation Implementation Basis:

1) Detection of bacterial growth: The growth of bacterial cells is determined by the light absorption value at 600 nm every 2 hours 2) PCN detection: The PCN produced by the bacterial cells in the bacteria solution is extracted with chloroform, concentrated, and then developed with hydrochloric acid, then the level of PCN produced by the bacteria is determined according to the light absorption value at 520 nm.

Specific Implementation:

According to this embodiment, the strain used is the *Pseudomonas aeruginosa* model strain PAO1; the clinical strain is isolated from Shaanxi Provincial People's Hospital and is isolated by the following method: Selective medium such as MacConkey agar (MAC) is inoculated to clinical specimen with normal flora or specimen collected from the environment; plain or blood agar media is inoculated to clinical specimen without normal flora such as blood, cerebrospinal fluid, puncture fluid, and etc. The oxidase of the bacteria is positive, can oxidatively decompose glucose and xylose, produce acid without producing gas, but do not decompose lactose and sucrose. Liquefied gelatin can decompose urea, nitrate reduction to produce nitrite and nitrogen is produced, indole negative without producing $H_2S$, arginine dihydrolase positive by using citrate. Based on the above physiological and biochemical characteristics, it is determined that the isolated strain is *Pseudomonas aeruginosa*.

In this study, shake flask culture is used to determine the effect of SNP on the growth of PAO1 and PCN biosynthesis. Multiple sets of samples with different concentrations of SNPs and one blank sample are used to study the effect of NO on cell growth and PCN synthesis. The final concentrations of SNPs in each group are 20, 60, 100, 140, 160, and 200 μM respectively. Samples are taken every 2 hours during shake flask culture for cell growth detection and PCN detection. The results are shown in A and B in FIG. 1. When the concentration of NO donor SNP is less than 100 μM, it has relatively small effect on the growth of PAO1 strain of *Pseudomonas aeruginosa*. From 20~100 μM, the synthesis of PCN decreases significantly with increasing concentrations of SNPs, and the ratio of PCN reduction to cell growth reduction at 60 μM is the largest. This shows that the SNP at 60 μM has the most significant inhibitory effect on the synthesis of PCN while having a relatively small effect on cell growth.

Figure 2:
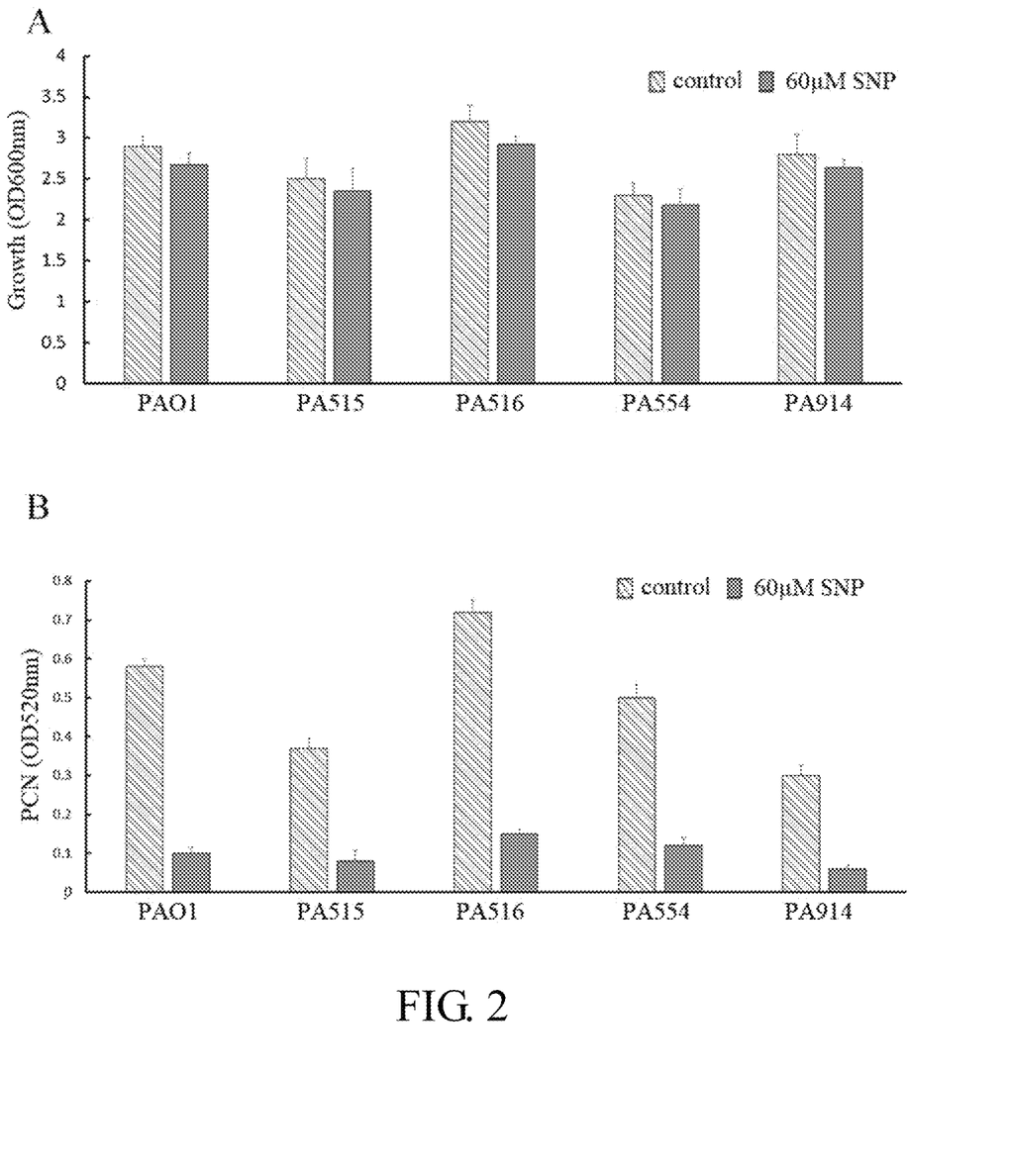
FIG. 2 shows the effect of 60 μm SNP on the growth of clinical isolation of *Pseudomonas aeruginosa* and PCN synthesis (A refers to the effect of 60 μm SNP on the growth of clinical isolation of *Pseudomonas aeruginosa*; B refers to the effect of 60 μm SNP on PCN synthesis of *Pseudomonas aeruginosa*)

Finally, the same experiments are performed on clinical isolations of *Pseudomonas aeruginosa* and similar results are obtained, thus demonstrating that co-culture with NO donor is universally applicable to the inhibition of PCN synthesis of *Pseudomonas aeruginosa* (see FIG. 2, where the effect on growth and inhibition of PCN synthesis are shown in A and B respectively).

Embodiment 3: Inhibition of the Target of NO Reductase (Nor) and Construction of Mutant Strains Lacking Nor Principle of implementation: Knocking out the Nor gene: First, construct a plasmid containing a Nor gene with inserted resistant fragment. At this point, Nor is unable to express because of the insertion of resistant fragment. This recombinant plasmid is introduced into PAO1 by triparental strain hybridization. Since the recombinant plasmid and the Nor-gene on the genome contain the same homology arms, the in-vitro inactivated Nor gene is inserted into the plasmid by homologous recombination to replace the Nor-gene on the genome so that the PAO1 cannot express the Nor gene and thus cannot synthesize Nor, thereby affecting the normal metabolism of NO and achieving NO accumulation.

Specific Implementation:

First construct the primers at the two ends of the Nor, then obtain the Nor gene by PCR. Then, through double digestion, connect and construct the recombinant plasmid with inserted Gm resistance Nor gene: nor-pexGm.

Figure 3:
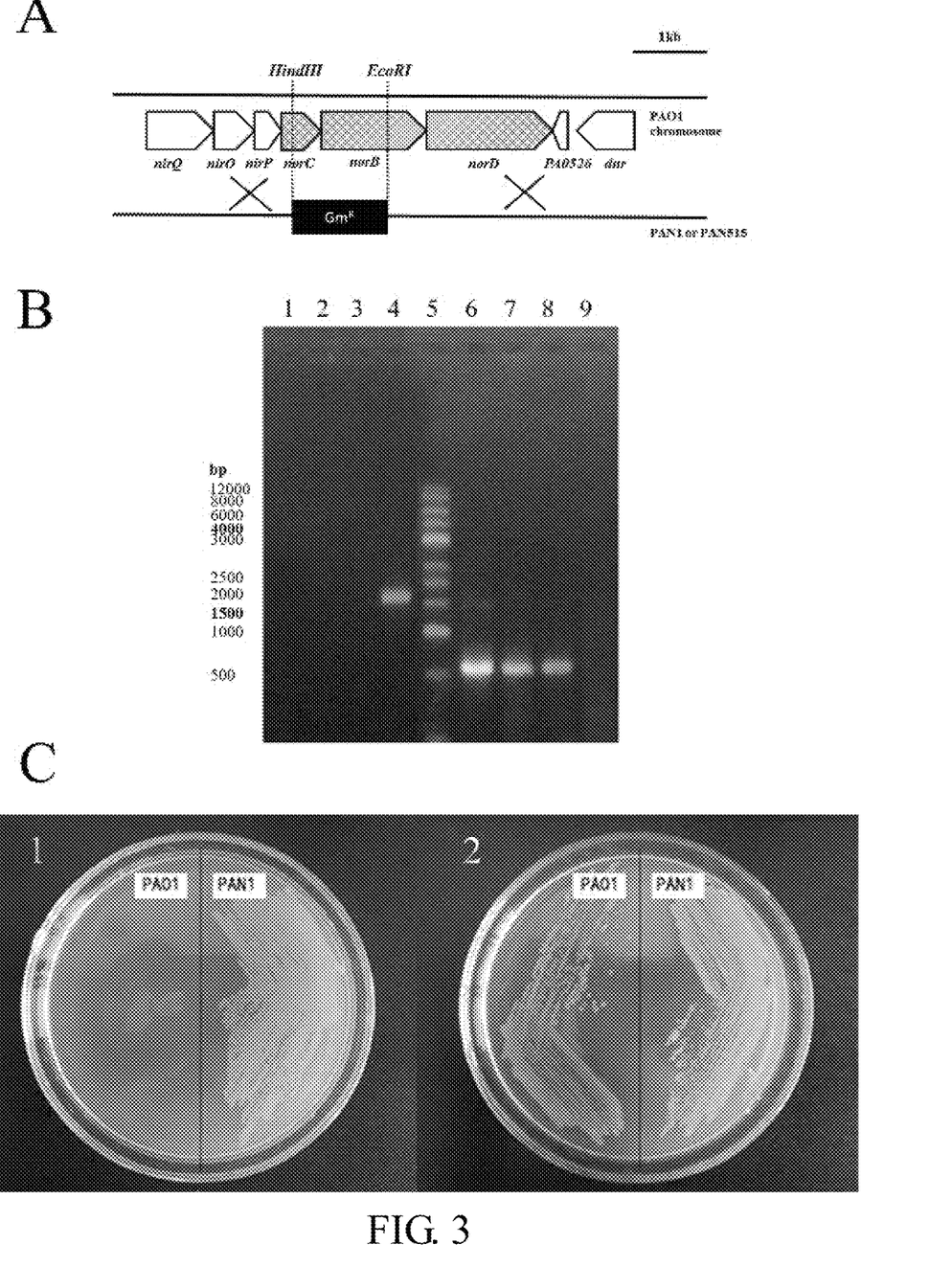
FIG. 3 illustrates Nor gene knockout and PCR, and resistance detection (A refers to gene structure of Nor and gen structure of Nor inserted with GM resistance; B is PCR validation of Δnor strain; C is the resistance verification of the Δnor strain)

After the target fragment nor-pexGm is obtained, purify and digest with different enzymes, then connected to the correspondingly digested plasmid pEX18-Amp or pEX18-Tc, transform to *E. coli* and screen positive clones with LB plates containing X-gal and AMP (50 μg/ml) or TET (15 μg/ml). After the enzyme digestion test (as shown in FIG. 3B), the lacZ-GM fragment derived from pZ1918-LacZ is further cloned into the PCR fragment of the recombinant plasmid (as shown in FIG. 3A, partial fragment in norBC) and transformed into *E. coli*. Screen and verify lacZ-GM fragment insertion direction by using LB solid plates containing GM (15 μg/ml), and finally construct into a recombinant plasmid for gene knockout (as shown in FIG. 3A, wherein the fragment associated with the Nor gene is: norBC-GM fragment).

After the recombinant plasmid is transformed into *E. coli*, homologous recombination occurs between the inserted fragment on the plasmid (norBC-GM fragment) and the homologous fragment on the genome of *Pseudomonas aeruginosa*, and triparental strain hybridization method is required. This plasmid is brought into the target strain PAO1 by the helper plasmid of the triparental strain hybrid.

The triparental strain hybridization process is as follows:

1. The donor strain (*E. coli* containing the recombinant plasmid, 15 μl/ml of GM) and the mediated bacteria (*E. coli* containing the helper plasmid pRK2013, 50 μg/ml of Kan) are cultured under 37° C. in 25 ml LB medium respectively, shake culture at 200 rpm for 14 hours, the recipient strain (*Pseudomonas aeruginosa*) is inoculated in 25 ml of LB medium and cultured at 42° C. and 200 rpm with shaking for 14 hours.

2. Transfer the bacteria into 50 ml sterile large centrifuge tube, centrifuge at 8000 rpm for 3 minutes, discarding the supernatant and then wash with 0.5 ml PBS for one time and transfer to 1.5 ml microcentrifuge tube. After weighing, resuspend the cells in PBS (concentration 500 μg/ml). Mix the above three bacterial suspensions in a new centrifuge tube in a ratio of 1:1:1 and gently blow the bacteria evenly.

3. Take 0.1 ml of well-mixed bacterial suspension and spot on the center of the LB solid plate. At the same time, spot 0.1 ml suspension of wild-type *Pseudomonas aeruginosa* as a negative control. Plates are placed in a 37° C. incubator to culture for 8-12 hours.

4. Resuspend the cells on the plate with 1 m PBS. After properly diluted, 100 μl is applied to PIA solid medium containing GM (150 μg/ml), place upside down position in a constant temperature incubator at 37° C. for 24 hours. At the same time, wild type *Pseudomonas aeruginosa* is also applied to a plate as a negative control.

Through a certain chance of homologous recombination in the bacteria, a mutant strain missing the entire Nor gene is obtained. Screen out this mutant strain by a series of screening methods such as PCR and resistance culture (as shown in C of FIG. 3).

Hybrid Strains Confirmation Experiments and Results:

A primary recombinant *Pseudomonas aeruginosa* can be grown on PIA plates containing GM and positive clones are selected for scribing on LB plates containing 10% sucrose. Secondary recombinant mutants are verified by TET sensitivity and PCR test. The results show that the PAO1Δnor strain is successfully constructed and labeled as PAN1. Referring to FIG. 3C, wherein 1 is a plate with GM resistance and only PAN1 strain grows on it, and 2 is a plate without antibiotic and both PAO1 and PAN1 strains can grow.

Similarly, in order to verify the universality, a clinical strain lacking the Nor gene is constructed simultaneously according to the above method.

Embodiment 4: Cultivation of ΔNor Mutants and Wild Strains by Shake Flask to Determine that the Selective Inhibition of Target Nor can Significantly Inhibit the Biosynthesis of *Pseudomonas aeruginosa* PCN and does not Stress the Growth of Bacteria Principle of Implementation: The role of NO reductase, Nor, is to convert intracellular NO to $N_2O$ so as to prevent excessive intracellular NO accumulation. Therefore, Δnor mutants will continue to accumulate endogenous NO and produce some biological effects. The present invention determines the effect of endogenous NO on its invasiveness factor PCN by comparing the growth and production of PCN in a Δnor mutant strain and a wild-type *Pseudomonas aeruginosa*.

Figure 4:
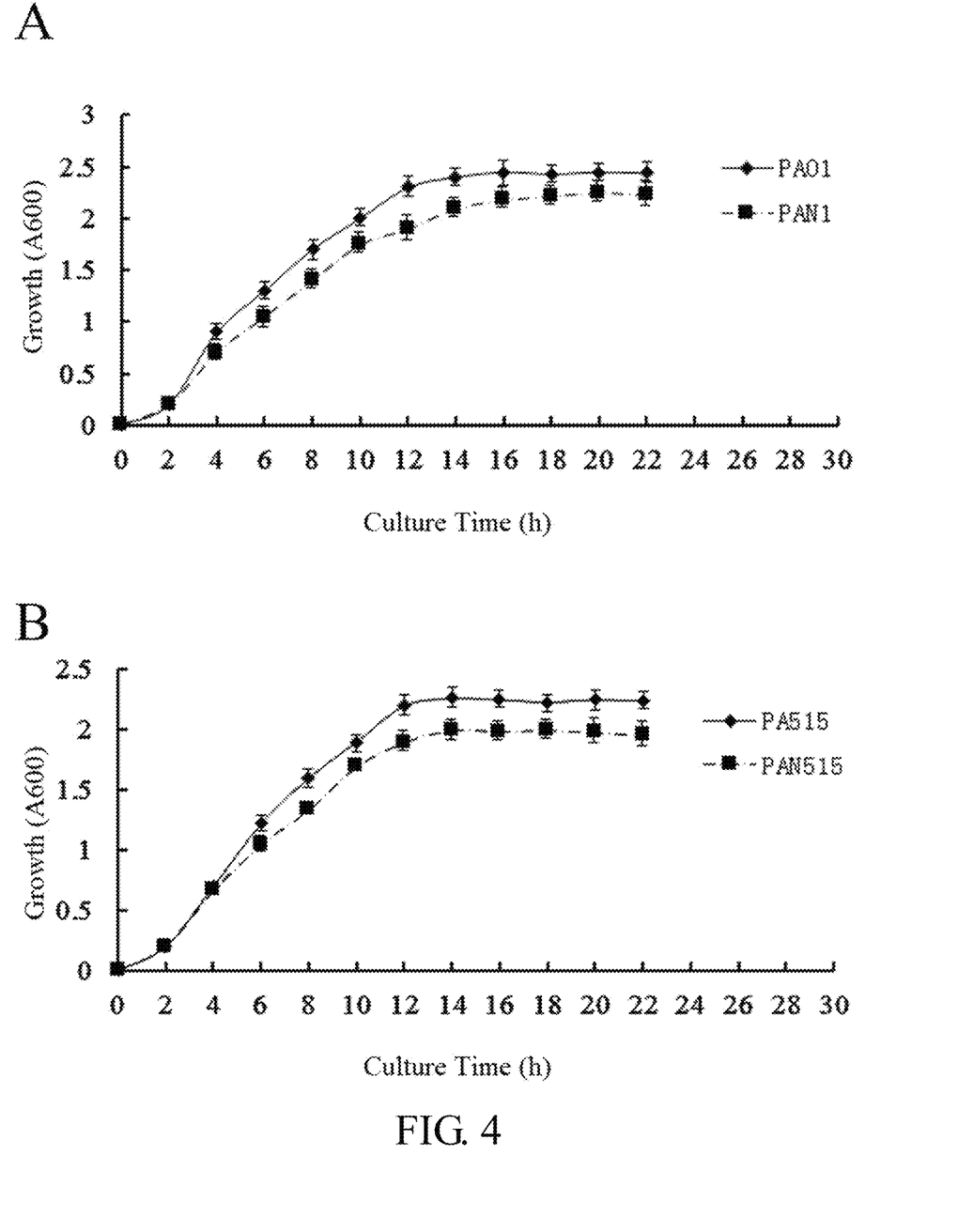
FIG. 4 shows the effect of nitric oxide reductase Nor on the growth of PAO1 and PA515 (A is the difference in the growth of PAO1 and its Δnor mutant PAN1; B is the difference in growth of P515 and its Δnor mutant PAN515)

Specific implementation: Culture both the PAO1Δnor mutant strain and the wild-type strain at the same time. Samples are taken every 2 hours for growth and PCN analysis. The results show that the mutant lacking Nor has relatively small changes in growth (the growth is reduced by 10%) but the synthesis of PCN is significantly reduced (PCN reduced by 84%, test results are shown in FIG. 4) when compared to the wild-type strain.

Figure 5:
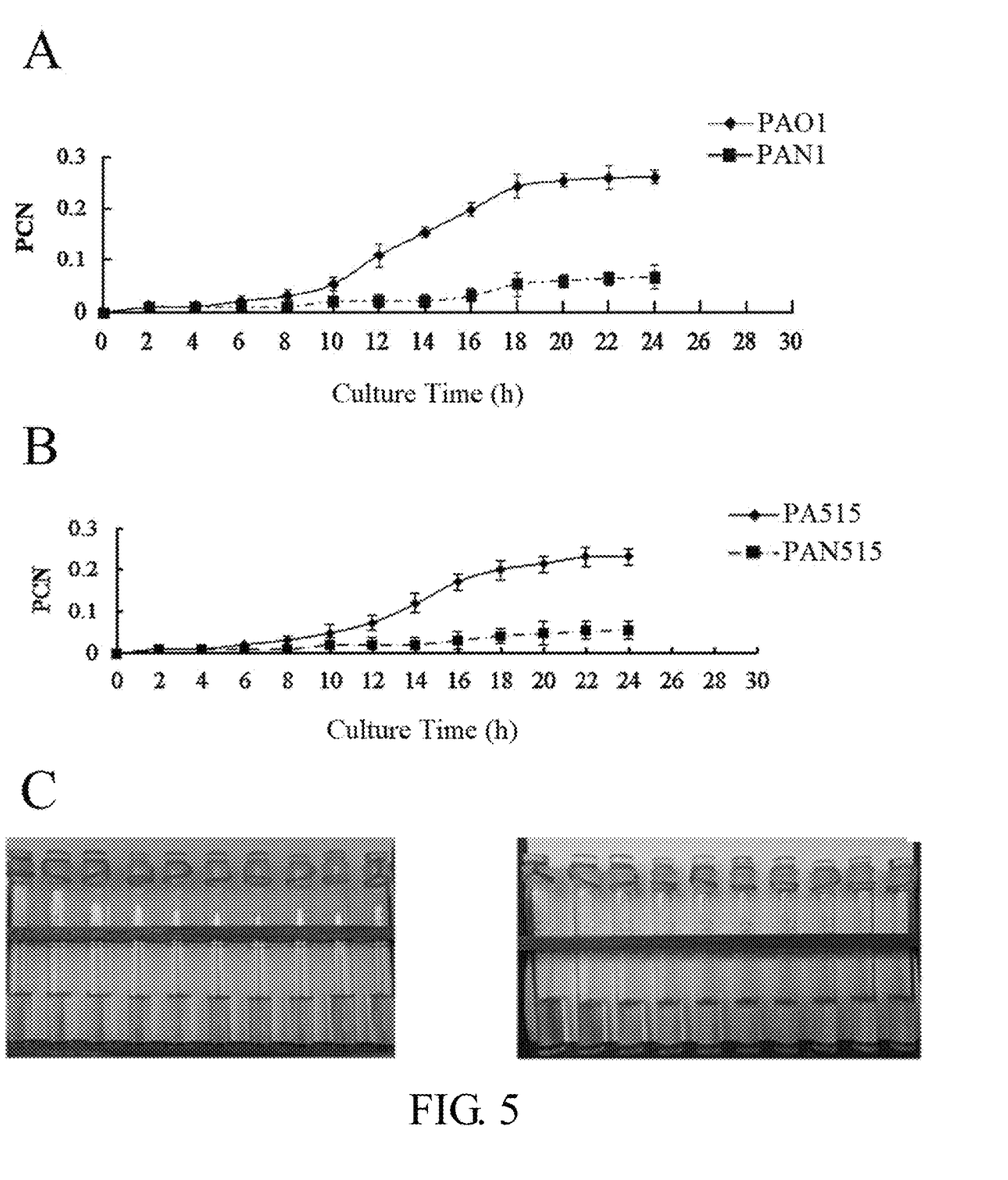
FIG. 5 shows the effect of nitric oxide reductase Nor on the PCN synthesis of PAO1 and PA515 (A is the difference in the PCN synthesis of PAO1 and its Δnor mutant PAN1; B is the difference in PCN synthesis of P515 and its Δnor mutant PAN515; C is the colorimetric comparison of extracted PCN)

In order to verify universality, the same experiment is performed on the Δnor mutant of a clinical strain PA515 and the wild strain, and similar results are obtained. This shows that endogenous accumulation of NO has a significant inhibitory effect on PCN synthesis while it has relatively small effect on the growth of *Pseudomonas aeruginosa* (FIG. 5).

Currently, studies have shown that the invasiveness of *Pseudomonas aeruginosa* can be reduced by inhibiting the synthesis of PCN. For example, Gee W. Lau et al. (Gee W. Lau et al. 2004) found that PCN produced by *Pseudomonas aeruginosa* plays a key role in the process of mice infection. In this study, three PCN synthetase mutants (ΔphzB1, ΔphzM, and ΔphzS) are constructed and the ability of these mutants to produce pyocyanin are significantly reduced. The subsequent animal experiments showed that the number of bacterial cells infected by these mutant strains in the lungs of mice and the mortality rate of mice are significantly lower than those of wild strains. The results of these studies indicate that the invasiveness of *Pseudomonas aeruginosa* can be reduced by inhibiting the synthesis of PCN. In combination with the above embodiment which determines that NO accumulation can significantly reduce the synthesis of *Pseudomonas aeruginosa* PCN, the present invention shows that NO accumulation can effectively reduce *Pseudomonas aeruginosa* invasiveness.

Embodiment 5: Determine the Selective Inhibition of Target Nor can Significantly Inhibit the Movement Ability of *Pseudomonas aeruginosa* PCN Through Motility and Mobility Tests Principle of implementation: *Pseudomonas aeruginosa* has a single-end single flagellum and several IV-type pilus at the end of the cell, both of which are important organ of movement. Flagella-mediated movement helps the bacteria to increase nutrient availability, escape toxic substances, transfer to appropriate hosts, and find suitable fixation sites. Flagella and type IV pili and their mediated movements are important pathogenic factors for *Pseudomonas aeruginosa*, both of which also play a crucial role in the initiation process of biofilms. The present invention investigates the effect on the movement activity of *Pseudomonas aeruginosa* when selectively inhibiting target Nor through motility and mobility tests.

Figure 6:
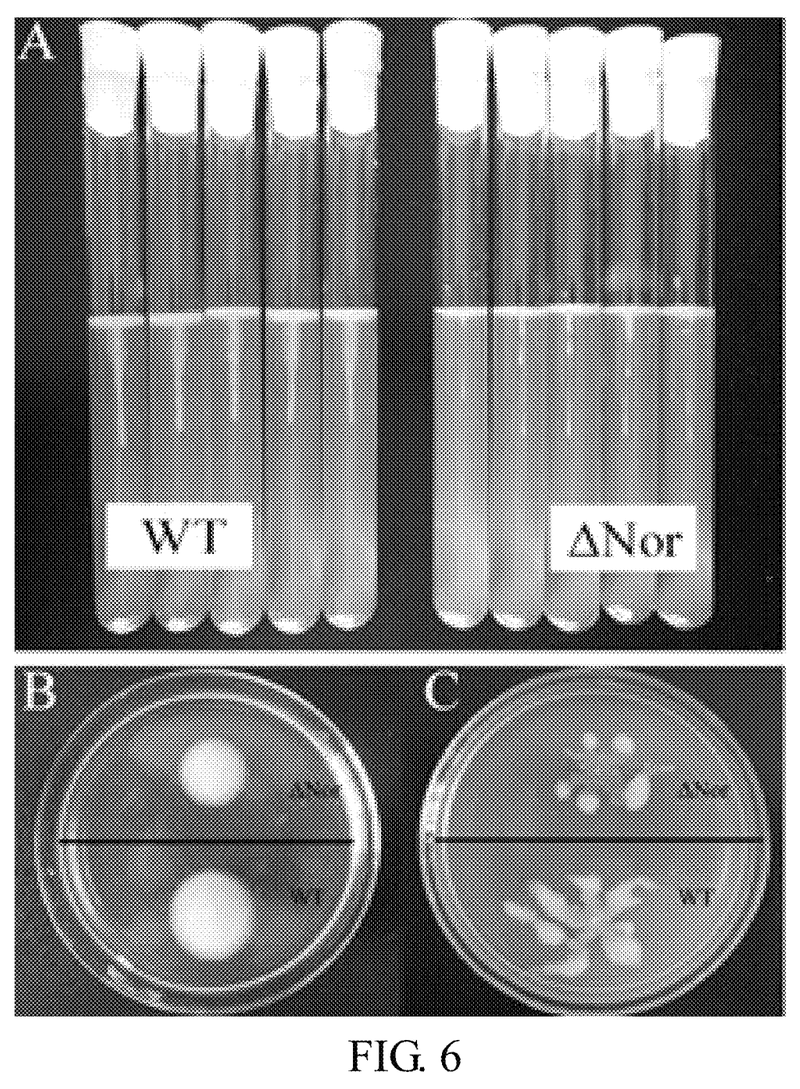
FIG. 6 shows the effect of Nor on the swimming activity and the driven property of PAO1, A: Test tube puncture swimming experiment result; B: a flat-plate swimming experiment result; C: flat-plate driven property experiment result.

Specific Implementation:

Swimming motility test: Place a thin layer of swimming motility detection medium in a Petri dish [10 g/L tryptone, 5 g/L NaCl, 0.3% agarose, pH 7.0], and dry overnight at room temperature. Pick PAO1 and PAO1-Δnor cultured overnight on LB agar medium by using sterilized toothpick and inoculated onto the surface of the swimming detection medium. Cover the culture dish with a layer of plastic wrap and incubate for 12-14 hours at 30° C. The bacteria relied on flagellar movement to grow around the inoculation site on the surface of the culture medium. The results show that the mutant strain lacking Nor significantly reduces the length of movement and reduces the number of bacteria capable of movement when compared with the wild strain, and the swimming motility is weakened. As shown in FIG. 6A, the comparison of WT and Δnor is illustrated.

Passive motility test: Place a thin layer of passive movement detection medium in a Petri dish [0.5% agarose, 8 g/L nutrient broth, 5 g/L glucose, pH 7.0], and dry overnight. Pick PAO1 and PAO1-Δnor cultured overnight on LB agar medium by using sterilized toothpick and inoculated onto the surface of the swimming detection medium. Cover the culture dish with a layer of plastic wrap and incubate for 12-14 hours at 30° C. Bacteria are affected by chemical tropism and relied on the movement of flagella and IV pili to form branched colonies on the surface of the medium. The results show that the mutant strain lacking Nor significantly reduces the plaque diameter and the passive movement ability when compared with the wild strain. As shown in FIGS. 6B and 6C, the comparison of WT and Δnor is illustrated.

Embodiment 6: Obtain Key Molecule and Key Site for NO Inhibition of PCN Synthesis by Using Quantitative Method of Phenyl Nitrosylation Modification Principle of Implementation: The present invention utilizes the irreversible avidin labeling (IBP) method to affinity enrich the SNO modified protein, analyzes the enriched SNO modified protein by mass spectrometry, and combines literature data to obtain a possible SNO modification key protein for NO inhibition on PCN synthesis.

Specific Implementation:

After processing *Pseudomonas aeruginosa* with NO donor treatment, collect the bacteria and obtain protein of bacteria by cleavage; use irreversible biotinylation procedure (IBP) for blocking, reduction and biotin labelling to produce Thionitrosylation-modified protein, which is then enriched and modified with Streptavidin. Process elution of modified protein by 2.5% SDS. After separation by gel electrophoresis, enzymatic hydrolysis of protein gel into peptides. Labeled modified protein peptides by mass spectrometric TMT reagents. Perform mass spectrometry after desalting. Identify the protein that undergoes SNO modification (nitrosylation) and quantitative changes after NO donor processing.

Protein modification studies show that: after treatment with NO donor SNP and GSNO (nitrosoglutathione), the overall SNO level of the PAO1 protein in *Pseudomonas aeruginosa* strains is increased significantly. The results of mass spectrometry show that a number of proteins related to the synthesis of *Pseudomonas aeruginosa* pathogenic factors have different degrees of SNO modification. The specific related proteins are shown in Table 6. The results show that NO inhibits the nitrosylation modification process of multiple key proteins that regulate protein control and protein synthesis, which is related to the synthesis of PCN, flagella and pilus.

TABLE 6

Ratio of target protein isotope 129/128 in relation to the *Pseudomonas aeruginosa* pathogenic factor in the modification sets

| Protein name | Protein category | 129/128 | Remark |
| --- | --- | --- | --- |
| RhlR | Regulation protein | 1.574 | PCN, flagella and pili |
| LasR | Regulation protein | 1.447 | PCN, flagella and pili |
| PhzB | Synthetic protein | 1.388 | PCN synthesis related |
| PhzA | Synthetic protein | 1.374 | PCN synthesis related |
| PilL | Synthetic protein | 1.338 | Pili synthesis related |
| FimL | Synthetic protein | 1.352 | Flagella synthesis related |

Note: 129 isotope labeled SNP treatment group with nitrosylated modified protein samples, 128 isotope marker control group with nitrosylated modified protein samples, the value of 129/128 of the target protein in the mass spectrometry test results represents: the relative change in the thiosylated modification of this protein in the SNP treatment group when compared with the control group.

Embodiment 7: Use of Animal Experiments to Study the In Vivo Effect of NO on Pathogenicity of *Pseudomonas aeruginosa*

Principle of Implementation: The role of NO reductase, Nor, is to convert intracellular NO to $N_2O$ to prevent excessive intracellular NO accumulation. Therefore, Δnor mutants will continue to accumulate endogenous NO and thus produce some biological effects. In the present invention, the effect of endogenous NO on the pathogenicity of *Pseudomonas aeruginosa* is determined by comparing the lethality of mice infected with Δnor mutants strain and wild strain of *Pseudomonas aeruginosa*.

Figure 7:
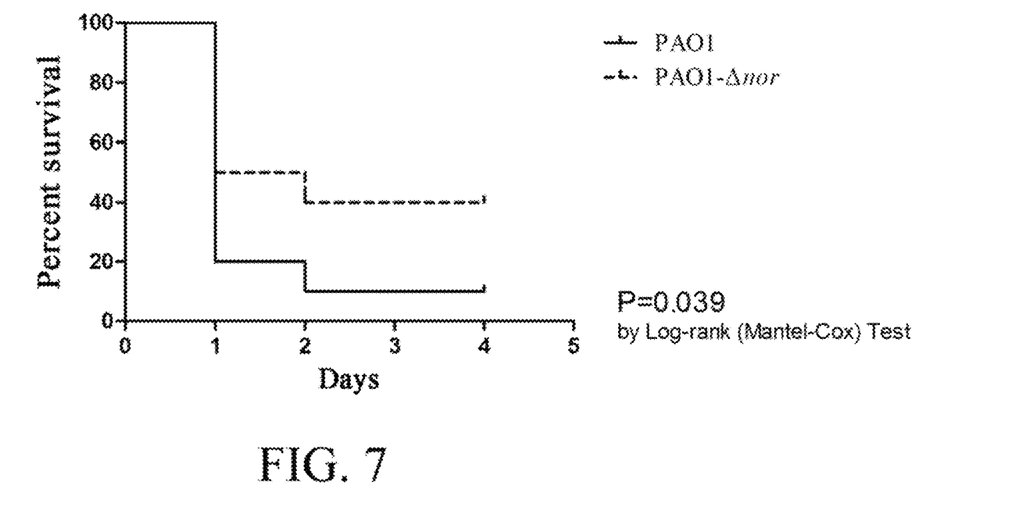
FIG. 7 shows the survival curves of mice infected with PAO1-Δnor and PAO1 at a bacteria concentration of OD600 nm=0.1 and inoculation volume of 500 μl.

Specific Implementation:
Take about 100 ml of PAO1 and PAO1-Δnor original bacteria solution. Centrifuge at 3000 r/min and take the precipitation. Dilute to OD600 nm 0.1 with sterile saline. Take 60 mice and randomly divide into three groups based on body mass, which are: PAO1 group, PAO1-Δnor group, and blank control group. 0.5 ml per group, intraperitoneal injection of bacterial suspension respectively. Observe and record the death of mice every day for five days continuously. Use Log-Rank method to examine the differences between different groups. The results are shown in FIG. 7. The results show that the survival rate of the PAO1-Δnor group is significantly higher than that of the PAO1 group ($P=0.039<0.05$ indicates significant difference between groups), and this shows that endogenous NO accumulation of in *Pseudomonas aeruginosa* can reduce the pathogenicity in the body.

Accordingly, the present invention provides the following applications:
The application of achieving NO accumulation through exogenous NO donor or endogenous NO metabolism blockage to reduce the production of the invasiveness factor of pyocyanin of *Pseudomonas aeruginosa* and/or reduce the motility of *Pseudomonas aeruginosa* under a living environment or a culture environment of *Pseudomonas aeruginosa*.

The application of NO donor compounds in the preparation of a medicament for reducing the invasiveness of *Pseudomonas aeruginosa*.

The use of a plasmid, vector or compound that blocks the NO metabolism of *Pseudomonas aeruginosa* in the preparation of a medicament for reducing the invasiveness of *Pseudomonas aeruginosa*.

Since NO reductase is a method to achieve NO accumulation, other methods can also achieve NO accumulation, its inhibition effect on PCN growth, its inhibition effect on *Pseudomonas aeruginosa* motility and its reduction effect of *Pseudomonas aeruginosa* invasiveness should have consistent results.

In particular, the application includes:
The realization of NO metabolism-blocking compounds in the form of antagonism, inhibition or blockade of NO metabolism in the preparation of a medicament for reducing the invasiveness of *Pseudomonas aeruginosa*.

The use of an enzyme, a carrier, or a compound that utilizes a key enzyme molecule in the NO metabolic pathway as a target or a recombinant target in the preparation of a medicament for reducing the invasiveness of *Pseudomonas aeruginosa*.

The application of medicament or carrier that utilizes NO reductase of *Pseudomonas aeruginosa* as a target in the preparation of a medicament for reducing the invasiveness of *Pseudomonas aeruginosa*.

NO metabolism related enzyme of *Pseudomonas aeruginosa* also include NO reductase, nitrate reductase, nitrite reductase and NO synthase. Therefore, these enzymes (NO reductase, nitrate reductase, nitrite reductase and NO synthase) can also be used as a target to control NO metabolism, therefore also applicable in the preparation of a medicament for reducing an invasiveness of *Pseudomonas aeruginosa*.

Cystic fibrosis (CF) is a fatal autosomal recessive genetic disorder caused by a functional defect in the CFTR protein encoded by a mutation in the cystic fibrosis transmembrane regulator (CFTR) gene. There are about 70,000 CF patients worldwide, of which the most common is Caucasian. Clinical data shows that the disease also has a certain incidence in our country. The mortality rate of CF is extremely high and the median survival time is short (analysis of the clinical features of Chinese cystic fibrosis). It is urgent to find effective treatment measures to improve the quality of life of CF patients. Spongy secretions from the lungs of CF patients block the airways and damage the cilia scavenging system, causing repeated or persistent bronchial infections. *Pseudomonas aeruginosa* is the most common colonizing bacteria in the airways. At the same time, *Pseudomonas aeruginosa* infection is also the most serious type of infection. According to statistics, more than 90% of patients suffered from pulmonary cystic fibrosis die from chronic infection with *Pseudomonas aeruginosa*.

*Pseudomonas aeruginosa* septicemia is a clinically serious systemic infection with serious illness and rapid progression. The mortality rate of *Pseudomonas aeruginosa* septicemia in foreign countries was 21.0% to 39.0, which was higher than *Staphylococcus aureus* septicemia. According to China's bacterial drug resistance monitoring network data from 2006 to 2007, it shows that *Pseudomonas aeruginosa* accounted for 4.7% of the pathogens of bloodstream infections, and ranked third among Gram-negative bacteria (2006-2007 Mohnarin bloodstream infection pathogen composition and drug resistance) Studying the prognostic factors of *Pseudomonas aeruginosa* septicemia is essential for clinical improvement of treatment success rate.

Studies have shown that the top 5 isolates of pathogenic bacteria obtained from CNS disease hospitals are: Studies have shown that the top 5 isolates of pathogenic bacteria obtained from CNS disease hospitals are: *Staphylococcus aureus* (23.7%), *Pseudomonas aeruginosa* (22.0%), *Acinetobacter baumannii* (18.6%), *Klebsiella pneumoniae* (8.5%), *Pseudomonas maltophilia* (6.8%). The foreign research statistics show that the clinical manifestations of central nervous system infection caused by *Pseudomonas aeruginosa* have a poor prognosis and the mortality rate is above 60%.

Therefore, based on an NO donor compound, the function of a medicament or carrier which utilizes NO reductase of *Pseudomonas aeruginosa* as a target to act on the invasiveness of *Pseudomonas aeruginosa* (reduce the production of the invasiveness factor of pyocyanin of *Pseudomonas aeruginosa* and/or reduce the motility of *Pseudomonas aeruginosa*) can also be applied to the preparation of medicament against pulmonary cystic fibrosis or *Pseudomonas aeruginosa* septicemia.

The above-presented embodiments are preferred examples for implementing the present invention, and the present invention is not limited to the above embodiments. Any non-essential additions and replacements made by those skilled in the art according to the technical features of the technical solutions of the present invention all belong to the protection scope of the present invention.

What is claimed is:

1. A method of reducing an invasiveness of *Pseudomonas aeruginosa*, characterized in that: said method comprises the steps of: under a living environment or a culture environment of *Pseudomonas aeruginosa*, achieving NO accumulation through an exogenous NO donor or an endogenous NO metabolism control, and reducing a production of an invasiveness factor of pyocyanin of *Pseudomonas aeruginosa*;
    simultaneously reducing a mediated motility of flagella and pili of *Pseudomonas aeruginosa*.

2. The method of reducing an invasiveness of *Pseudomonas aeruginosa* according to claim 1, characterized in that: said exogenous NO donor comprises a compound capable of directly or indirectly supplying NO to *Pseudomonas aeruginosa*, said exogenous NO donor is present in the living or in the culture environment of *Pseudomonas aeruginosa*.

3. The method of reducing an invasiveness of *Pseudomonas aeruginosa* according to claim 1, characterized in that: said endogenous NO metabolism control includes inhibition, blocking, or enhancement of NO metabolism-related enzyme.

4. The method of reducing an invasiveness of *Pseudomonas aeruginosa* according to claim 3, characterized in that: said blocking of said endogenous NO metabolism comprises the steps of: cloning a plasmid or vector that is capable of recombining with NO metabolism-related enzyme and causing loss of function of NO metabolism-related enzyme into *Pseudomonas aeruginosa*; or employing an inhibitor of NO metabolism-related enzyme such that the activities of enzyme are reduced or lost so as to achieve NO accumulation in *Pseudomonas aeruginosa*; or employing genetic recombination or agonists to enhance the enzyme that favor production of endogenous NO to achieve NO accumulation in *Pseudomonas aeruginosa*.

5. The method of reducing an invasiveness of *Pseudomonas aeruginosa* according to claim 1, wherein said method is used to provide a target for reducing the invasiveness of *Pseudomonas aeruginosa*, said target comprises intracellular gene locus associated with NO metabolism in *Pseudomonas aeruginosa* and enzymes associated with NO metabolism;
    said intracellular gene locus associated with NO metabolism and said enzymes associated with NO metabolism are inhibited or activated to achieve NO accumulation, thereby reducing production of the invasiveness factor of pyocyanin of *Pseudomonas aeruginosa* and reducing a motility of *Pseudomonas aeruginosa*.

6. The method of reducing an invasiveness of *Pseudomonas aeruginosa* according to claim 1, wherein said method is used to provide an application of NO donor compound in the preparation of a medicament for reducing the invasiveness of *Pseudomonas aeruginosa*.

7. The method of reducing an invasiveness of *Pseudomonas aeruginosa* according to claim 1, wherein said method is used to provide an application of a medicament or a carrier which utilizes NO metabolism related enzyme of *Pseudomonas aeruginosa*, which comprises NO reductase, nitrate reductase, nitrite reductase, and NO synthase, as a target in the preparation of a medicament for reducing an invasiveness of *Pseudomonas aeruginosa*.

8. The method of reducing an invasiveness of *Pseudomonas aeruginosa* according to claim 1, wherein a concentration of said exogenous NO donor has a range of 20 μM-60 μM.

9. The method of reducing an invasiveness of *Pseudomonas aeruginosa* according to claim 8, wherein said exogenous NO donor is sodium nitroprusside.

* * * * *